United States Patent [19]
Hall et al.

[11] Patent Number: 5,912,275
[45] Date of Patent: Jun. 15, 1999

[54] PROCESS FOR DEPOLYMERIZING POLYESTER

[75] Inventors: Stephen Dana Hall; Richard Redfearn Hepner; Robert Everett Michel, all of Wilmington, N.C.; Donald Richard Wheatcraft, Jr., Hendersonville, Tenn.; George Malcolm Williamson, Wilmington, N.C.

[73] Assignee: E. I. du Pont de Nemours and Company, Wilmington, Del.

[21] Appl. No.: 08/940,595

[22] Filed: Sep. 30, 1997

[51] Int. Cl.$^6$ ...................................................... C08J 11/10
[52] U.S. Cl. .......................... 521/48; 521/48.5; 528/308.1; 528/491; 528/495; 528/502 R
[58] Field of Search ................. 521/48, 48.5; 528/308.1, 528/491, 495, 502 R

[56] References Cited

U.S. PATENT DOCUMENTS

| 2,884,443 | 4/1959 | Siggel et al. ............................. 260/475 |
| 5,051,528 | 9/1991 | Naujokas et al. .......................... 560/78 |
| 5,391,263 | 2/1995 | Hepner et al. ............................. 203/51 |
| 5,393,916 | 2/1995 | Gamble et al. ............................ 560/78 |
| 5,504,122 | 4/1996 | Michel et al. ......................... 521/48.5 |

FOREIGN PATENT DOCUMENTS

484963 A2  5/1992  European Pat. Off. .

*Primary Examiner*—James J. Seidleck
*Assistant Examiner*—Olga Asinovsky

[57] ABSTRACT

Polyester is depolymerized by methanolysis and methanol is recovered in a process that uses methyl benzoate and/or p-methyltoluate as an azeotropic agent while the methanol is present.

4 Claims, 1 Drawing Sheet

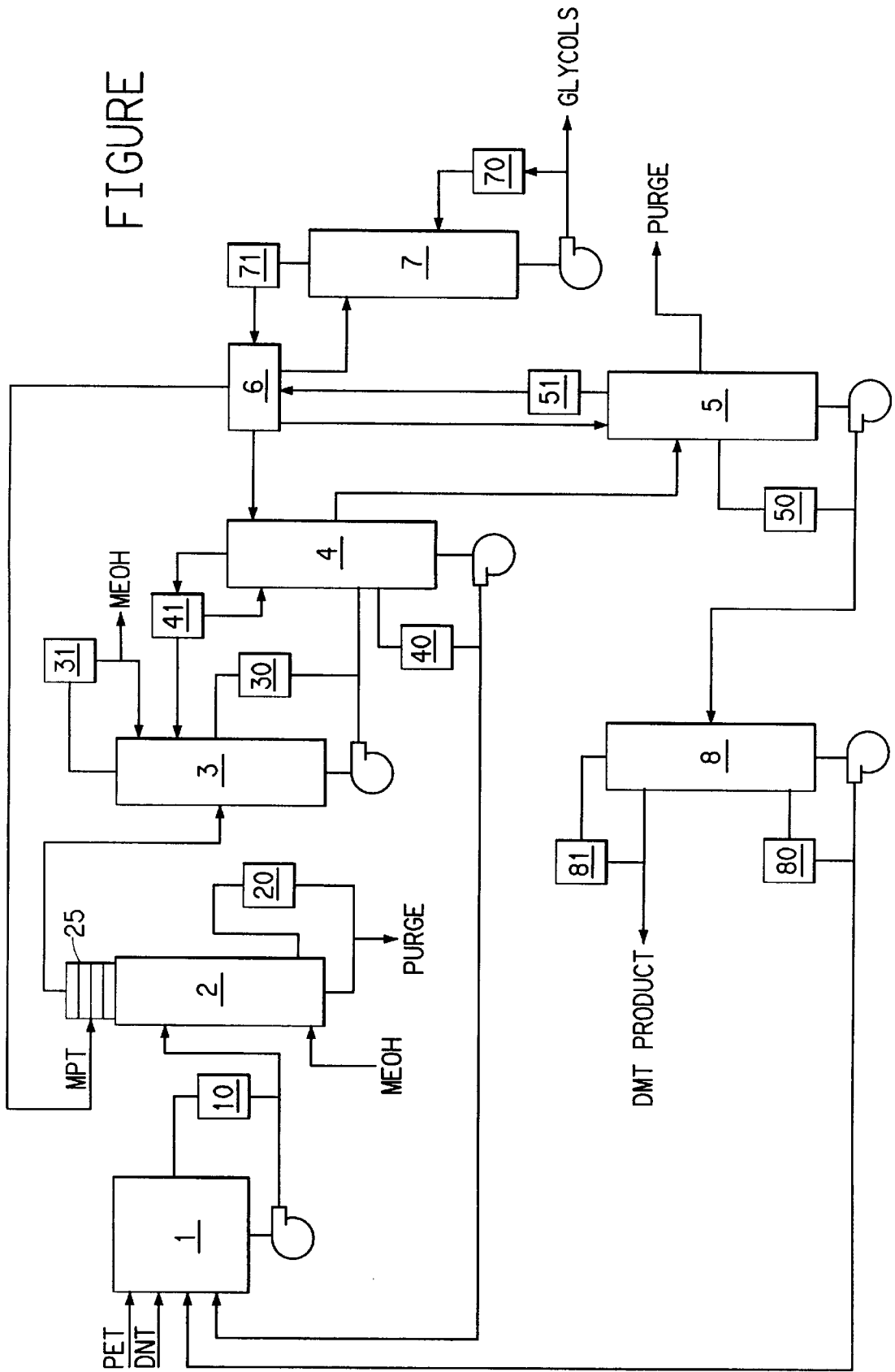

PROCESS FOR DEPOLYMERIZING POLYESTER

FIELD OF INVENTION

This invention concerns improvements in and relating to a process for depolymerizing polyester, and more particularly for depolymerizing polyester by methanolysis.

BACKGROUND

Several prior suggestions have been made for recovering methyl esters of aromatic acids and glycols from thermoplastic polyester scrap using methanolysis, i.e., treating the polyester polymer with methanol, such as U.S. Pat. Nos. 5,504,122 (Michel et al), 5,393,916 (Gamble et al), 5,391,263 (Hepner et al), 5,051,528 (Naujokas et al), and EP 484,963 (DuPont-Michel), and in art references cited therein. Further improvements would be desirable in view of the commercial importance of polyester polymers and the increasing need to recover their chemical precursors from polyester scrap. Ethylene terephthalate polymers have been the polyester polymers that have been used commercially for the most part, and so these polymers and their chemical precursors, ethylene glycol (EG), terephthalic acid (TPA) and dimethyl terephthalate (DMT), so are the polyester polymers mainly discussed hereinafter, but the invention is believed applicable to other polyester polymers, for instance trimethylene glycol terephthalate (sometimes referred to as 3G-T, sometimes as PTT) and tetramethylene glycol terephthalate (4G-T).

Hepner et al U.S. Pat. No. 5,391,263 concerns a process for the separation of glycols from dimethyl terephthalate (DMT) involving distillation using methyl benzoate and/or the methyl ester of p-toluic acid (MPT) as an azeotropic agent. In particular, that process was applied to a mixture formed by the treatment of waste polyester with methanol to form DMT, EG and diethylene glycol (DEG) in which process, referring to Hepner's drawing, polyethylene terephthalate (PET) and DMT were heated and the resulting molten polymer mixture was treated with methanol (MEOH) vapor and depolymerized in a (methanolysis) reactor, from the reflux section of which a vapor mixture of MEOH, EG, DMT and DEG was passed to a methanol removal column. After removal of MEOH, the (rest of the) mixture was passed to an azeotrope column, and was treated with the azeotropic agent (MPT and/or methyl benzoate), the DMT being removed from the azeotrope column as bottoms and the resulting azeotropes being taken overhead to a vessel for separation into two phases, namely a phase rich in the azeotropic agent, which could be recycled to the azeotrope column, and a phase rich in glycols, which was passed to a distillation column to recover the desired glycols as bottoms and the azeotropic agent overhead.

SUMMARY OF THE INVENTION

We have now found, according to the present invention, advantages in such a process may be obtained by adding azeotropic agent earlier than was disclosed by Hepner in U.S. Pat. No. 5,391,263, in other words before removal of the methanol, i.e., while significant amounts of methanol are still present.

Accordingly, there is provided a process for depolymerizing polyester, involving a step (A) of treating the polyester with methanol at elevated temperature in a zone to provide a mixture, followed by one or more steps for recovering dimethyl terephthalate (DMT) and glycol, and including a step (B) of recovering methanol from the mixture resulting from step (A), in which process there is used an azeotropic agent selected from the group consisting of methyl p-toluate, methyl benzoate and mixtures of methyl p-toluate and methyl benzoate, wherein the improvement comprises adding said azeotropic agent to the process no later than in step (B).

The azeotropic agent is preferably added in step (A), and preferably at the top of the methanolysis reactor, and especially so that the azeotropic agent and the mixture resulting from step (A) reflux as they leave the zone in step (A).

BRIEF DESCRIPTION OF THE DRAWING

The FIGURE is a diagrammatic view of a process for depolymerizing polyester according to a preferred embodiment of the present invention.

DETAILED DESCRIPTION

As indicated, the present invention is an improvement in prior suggestions for depolymerizing polyester, such as have been disclosed in EP 484,963 (DuPont, Michel), Naujokas et al U.S. Pat. No. 5,051,528, Gamble et al U.S. Pat. No. 5,393,916, Michel et al U.S. Pat. No. 5,504,122, and especially, Hepner et al U.S. Pat. No. 5,391,263, each of which is hereby included herein by reference to avoid repetition. The distinctions from Hepner will be apparent hereinafter, especially with regard to a preferred embodiment of the invention that is now described with reference to the accompanying drawing.

PET and DMT are fed into a heated vessel 1, where the PET is dissolved. The resulting molten solution is fed to reactor 2, where it is treated with methanol (MEOH) vapor, i.e., methanolysis occurs. The azeotropic agent (such as MPT) is fed to a reflux section 25 that is located at the top of reactor 2. The vapor that emerges from the top of the reflux section is a mixture of the azeotropic agent, MEOH, EG, DMT, DEG and methyl 2-hydroxyethyl terephthalate (MHET) and is passed to column 3 for removal of methanol. In column 3, after removal of most of the methanol overhead, the bottoms from methanol removal column 3 are fed into "Heavies" column 4, where the rest of the methanol is removed overhead, a side-draw consisting of the azeotropic agent, DMT, EG and DEG, is fed to column 5, and the bottoms, consisting of DMT and MHET, are returned to vessel 1. From column 5, the azeotropes of the glycols and the azeotropic agent are taken overhead and fed to vessel 6, where they are allowed to separate into two phases, as taught by Hepner. Unlike what Hepner taught, however, the phase that is rich in azeotropic agent is fed to act as reflux at top of reactor column 2. The phase that is rich in glycols is passed to column 7, where the glycols are recovered as bottoms (as taught by Hepner) and the azeotropic agent is recovered overhead. Make-up azeotropic agent may be fed to the reflux at the top of reactor column 2 or elsewhere appropriate into the system. Purges may be taken as shown, as a side-draw from column 5, and from column 2. The bottoms from column 5 are fed to a distillation column 8, where DMT product is removed overhead and the bottoms, consisting mostly of DMT with some MHET, and possibly some bis-2-hydroxyethyl terephthalate (DHET), are returned to vessel 1.

In the drawing some heaters for the vessels are illustrated and designated, respectively, as 10, 20, 30, 40, 50, 70 and 80, and some condensers, respectively, as 31, 41, 51, 71 and 81.

To demonstrate advantages of the present invention, the following comparative tests were carried out using a small scale distillation column having 15 trays, all parts and percentages being by weight.

COMPARATIVE TEST

A. The still pot was charged with 150 parts of DMT, 100 parts of EG, 100 parts of MEOH, and 150 parts of MPT. The pot was heated to boiling at atmospheric pressure and distillation was begun. All of the methanol was removed by distillation. No solids formed in the column even as the head reached 160° C.

B. In contrast, to demonstrate what can happen if the azeotropic agent is only added after removal of the methanol, when the still pot was charged with only the DMT, EG and MEOH, in the same amounts, without any MPT, and heated similarly to distill the MEOH, after removal of about 98% of the MEOH, solids were observed forming in the lower half of the column. These solids plugged the column and distillation had to be stopped.

We believe that this occurred because the physical situation in the trayed section (corresponding to the reflux section at the top of the methanolysis reactor) is entirely different from that usually confronted during distillation. The presence of excess methanol can lead to a high concentration of non-condensible solids. Addition of sufficient of an external refluxing agent, however, surprisingly has been found to resolve this difficulty according to the present invention. This can be seen from the following calculations in Table I to show the effect of 10% by weight MPT reflux on the relative concentrations by weight of DMT, MHET and DHET in the vapor exit stream from the methanolysis reactor 2.

TABLE 1

| COMPONENT | WITHOUT MPT | WITH MPT | % Δ |
|---|---|---|---|
| DMT | 91.46 | 93.95 | +2.7 |
| MHET | 7.04 | 6.05 | −14 |
| DHET | 1.50 | <0.01 | >−99 |

Table I indicates almost complete removal of all DHET by use of 10% MPT reflux, and 14% reduction of MHET. By analogy with such DHET reduction, no metal salt carry over from the reactor would also be expected; avoidance of this is highly desirable.

Similarly, relative concentrations of the same components are calculated in Table II for the Feed into and Bottoms from "Heavies" column 4.

TABLE II

| COMPONENT | FEED | BOTTOMS | % Δ |
|---|---|---|---|
| DMT | 93.95 | 99.5 | +5.6 |
| MHET | 6.05 | >0.05 | −99 |
| DHET | <0.01 | 0 | — |

Table II indicates almost 100% removal of MHET (as well as the DHET).

What is claimed is:

1. An improvement in a process for depolymerizing polyester, involving a step (A) of treating the polyester with methanol at elevated temperature in a zone to provide a mixture, followed by one or more steps for recovering dimethyl terephthalate and glycol, and including a step (B) of recovering methanol from the mixture resulting from step (A), in which process there is used an azeotropic agent selected from the group consisting of methyl p-toluate, methyl benzoate and mixtures of methyl p-toluate and methyl benzoate, wherein the improvement comprises adding said azeotropic agent to the process no later than in step (B).

2. A process according to claim 1, wherein the azeotropic agent is added in step (B).

3. A process according to claim 1, wherein the azeotropic agent is added in step (A).

4. A process according to claim 3, wherein the azeotropic agent and said mixture reflux as they leave said zone in step (A).

* * * * *